(12) United States Patent
Teitelbaum et al.

(10) Patent No.: US 8,080,579 B2
(45) Date of Patent: Dec. 20, 2011

(54) COMPOSITIONS AND METHODS FOR TREATMENT OF INFLAMMATORY BOWEL DISEASE

(75) Inventors: Daniel H. Teitelbaum, Ann Arbor, MI (US); Barbara E. Wildhaber, Geneva (CH); Hua Yang, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 0 days.

(21) Appl. No.: 11/542,576

(22) Filed: Oct. 3, 2006

(65) Prior Publication Data

US 2007/0123499 A1 May 31, 2007

Related U.S. Application Data

(60) Provisional application No. 60/723,031, filed on Oct. 3, 2005, provisional application No. 60/775,055, filed on Feb. 21, 2006.

(51) Int. Cl.
*A61K 31/40* (2006.01)
(52) U.S. Cl. ...................................... 514/423
(58) Field of Classification Search ................ 424/78.38
See application file for complete search history.

(56) References Cited

U.S. PATENT DOCUMENTS

| | | | |
|---|---|---|---|
| 4,344,949 A | 8/1982 | Hoefle et al. | |
| 4,473,575 A | 9/1984 | Watthey | |
| 6,267,990 B1 | 7/2001 | Fischer et al. | |
| 6,413,494 B1 * | 7/2002 | Lee et al. | 424/9.1 |
| 2005/0020654 A1 * | 1/2005 | Pershadsingh et al. | 514/394 |
| 2005/0256095 A1 * | 11/2005 | Ahlem et al. | 514/178 |
| 2005/0271596 A1 * | 12/2005 | Friedman et al. | 424/45 |
| 2006/0167012 A1 * | 7/2006 | Noble et al. | 514/255.02 |

FOREIGN PATENT DOCUMENTS

| | | |
|---|---|---|
| EP | 79-022 | 2/1982 |
| EP | 60668 | 8/1982 |
| EP | 80822 | 11/1982 |
| GB | 2103614 | 8/1982 |

OTHER PUBLICATIONS

Odze, R. "Diagnostic Problems and Advances in Inflammatory Bowel Disease". Modern Pathology. 2003. vol. 16. No. 4. pp. 347-358.*
The Merck Manual, 17th edition (1999), p. 302-307.*
Kirsner, J. B., et al. (eds), Inflammatory Bowel Disease, 3rd ed., Lea and Febiger, Philadelphia (1988). This is a book and is not being supplied at this time.
Zipser, R. D., (ed.), "Mediators of Inflammation in Inflammatory Bowel Diseaase", Dig. Dis. Sci., 33 Suppl.:1S-87S (1988).
Schappi, et al., "Colitis in chronic granulomatous disease" Arch. Dis. Child., 1984:147-151 (2001).
Noguchi, et al., "Comparison of Acute Hemodynamic Effects of MC-838, a New Angiotensin-Converting Enzyme Inhibitor, with Captopril in Anesthetized Dogs", Jap. J. Pharmacol. 40(3):373-80 (1986).
Nussberger, et al., "Repeated Administration of the Converting Enzyme Inhibitor Cilazapril to Normal Volunteers", J. Cardiovasc. Pharmacol. 9(1):39-44 (1987).
Attwood, et al., "New potent inhibitors of angiotensin converting enzyme", FEBS Lett. 165(2):201-6 (1984).
Takata, et al., "A Comparison of the Actyivity of the Angiotensin Converting Enzyme Inhibitors SQ 14 225, SA 446 and MK 421", Clin. Exp. Pharmacol. Physiol. 10:131 (1983).
Acta. Pharmacol. Toxicol. 59 (Supp. 5):1:224 (1986).
Acta. Pharmacol. Toxicol. 59 (Supp. 5):2:342 (1986).
Sybertz, et al., "Angiotensin-Converting Enzyme Inhibitory Activity of SCH 31846, a New Non-Sultbydryl Inhibitor", J. Cardiovasc. Pharmacol. 5(4):643, 655 (1983).
Lees, "The Haemodynamic and Humoral Effects of Treatment for One Month with the Angiotensin Converting Enzyme Inhibitor Perindopril in Salt Replete Hypertensive Patients", Eur. J. Clin. Pharmacol. 31(5):519-24 (1987).
Kim, et al., "(Mercaptopropanoyl)indoline-2-carboxyliAc cids and Related Compounds as Potent Angiotensin Converting Enzyme Inhibitors and Antihypertensive Agents", J. Med. Chem. 26:394-403 (1983).
Baum, et al., "Antihypertensive Activity of SCH 31846, a Non-Sulfhydryl Angiotensin-Converting Enzyme Inhibitor", J. Cardiovasc. Pharmacol. 5(4):655 (1983).
Davies et al., Br. J. Clin. Pharm (1984), 18, 215S-229S, submitted herewith, p. 215S-216S.
Elung-Jensen et al., Eur J Clin Pharmacol, 2005, 61:87-96.

* cited by examiner

*Primary Examiner* — Phyllis G. Spivack
(74) *Attorney, Agent, or Firm* — Casimir Jones S.C.

(57) ABSTRACT

The present invention provides compositions and methods for treating inflammatory bowel disease. In particular, the present invention provides methods of therapeutically treating symptoms of inflammatory bowel disease using compositions comprising an angiotensin converting enzyme (ACE) inhibitor and polyethylene glycol.

17 Claims, 11 Drawing Sheets

ACE and epithelial cell proliferation

COMPOSITIONS AND METHODS FOR TREATMENT OF INFLAMMATORY BOWEL DISEASE

This invention claims priority to U.S. Provisional Patent Application Nos. 60/723,031, filed Oct. 3, 2005, and 60/775,055, filed Feb. 21, 2006, each of which is hereby incorporated by reference in its entirety.

FIELD OF THE INVENTION

The present invention provides compositions and methods for treating and preventing inflammatory bowel disease and other gastrointestinal disorders (e.g., mucositis, radiation induced enteritis, and short bowel syndrome). In particular, the present invention provides methods of treating and preventing symptoms of inflammatory bowel disease and other gastrointestinal disorders using compositions comprising an angiotensin converting enzyme (ACE) inhibitor and polyethylene glycol.

BACKGROUND OF THE INVENTION

Inflammatory Bowel Disease (IBD) refers to a group of gastrointestinal disorders characterized by a chronic non-specific inflammation of portions of the gastrointestinal tract. Ulcerative colitis and Crohn's Disease are the most prominent examples of IBD in humans. They are associated with many symptoms and complications, including growth retardation in children, rectal prolapse, blood in stools (e.g., melena and/or hematochezia), wasting, iron deficiency, and anemia (e.g. iron deficiency anemia and anemia of chronic disease or of chronic inflammation).

The etiology (or etiologies) and pathogenesis of IBD are still unclear. Previous understanding of the pathogenesis was limited to a three-stage process: (a) an irritant, which could be an immune process or infectious agent, activates (b) leukocytes which release enzymes such as pro-inflammatory cytokines (particularly tumor necrosis factor alpha (TNA-$\alpha$), proteases and inflammatory mediators such as histamine, serotonin and prostaglandins, and (c) these products cause edema, pain, heat and loss of function (See, e.g., Wyngaarden and Smith (eds.) Cecil's Textbook of Medicine (W. B. Saunders Co. 1985), Berkow (ed.). The Merck Manual of Diagnosis and Therapy (Merck Sharp & Dohme Research Laboratories, 1982), and Harrison's Principles of Internal Medicine, 12th Ed., McGraw-Hill, Inc. (1991)).

Numerous theories implicate multiple factors leading up to IBD including genetic predisposition, environmental factors, infectious agents and immunologic alterations (See e.g., Kirsner, J. B., et al. (eds), Inflammatory Bowel Disease, 3rd ed., Lea and Febiger, Philadelphia (1988); Zipser, R. D., (ed.), Dig. Dis. Sci., 33 Suppl.:1S-87S (1988)). The immunologic alterations in IBD appear to be autoimmune in nature, with autoantibodies and lymphocyte-cytotoxicity directed against intestinal epithelial cells. However, even the latest developments in the immunologic aspects of the pathogenesis of IBD cannot answer the basic question, i.e., whether the detected changes in humoral and cellular immunity reflect a primary defect or secondary response to injury.

Treatment for IBD currently includes steroids, sulphasalazine and its derivatives, and immunosuppressive drugs such as cyclosporin A, mercaptopurine and azathioprine. Such therapies are directed toward suppression of the general immune response. These approaches may result in poor success, and have little or no selectivity. As well, these approaches can be accompanied by unwanted and sometimes dangerous consequential side effects.

Thus, there exists a need for effective treatment, both prophylactic and therapeutic, for IBD and related conditions. Such a therapy should be specific and should not be accompanied by unwanted side effects.

SUMMARY OF THE INVENTION

The present invention provides methods for treating and preventing inflammatory bowel disease and related conditions (e.g., short bowel syndrome). In particular, the present invention provides methods of treating symptoms of inflammatory bowel disease and related conditions using angiotensin converting enzyme (ACE) inhibitors.

Accordingly, the present invention provides a method of treatment, comprising providing a subject having a symptom of inflammatory bowel disease or a related condition and a therapeutic composition comprising an angiotensin converting enzyme inhibitor and polyethylene glycol, and; administering the composition to the subject under conditions such that the manifestations of the condition are reduced. It is not intended that the present invention be limited to any particular subject. Indeed, a variety of subjects are contemplated. In one embodiment, the subject is a mammal. In a preferred embodiment, the subject is a human. In some embodiments, the polyethylene glycol is 1000 molecular weight. In some embodiments, the polyethylene glycol is greater than 1000 molecular weight. In some embodiments, the polyethylene glycol is less than 1000 molecular weight. The present invention is not limited to compositions comprising ACE inhibitors and PEG. Indeed, any composition that is generally non-absorbable in mucosa that is non-inflamed and intact (e.g., PEG, PEG-like compounds, and other biologically inert and compatible compounds) but that can pass into an intestinal wall exhibiting inflammation and/or ulcerations (e.g., during a state of active inflammation) can be included in a composition comprising and ACE inhibitor (e.g., thereby facilitating the transport of the ACE inhibitor into an inflamed site).

In some embodiments, the composition comprising an angiotensin converting enzyme inhibitor and polyethylene glycol is co-administered with a corticosteroid. In some embodiments, the corticosteroid is prednisone. In some embodiments, uses include therapeutic, research and drug screening.

In some preferred embodiments, compositions of the present invention are administered rectally (e.g., as an enema). The present invention is not limited to any particular route of administration. Indeed, a variety of administrative routes are contemplated to be useful for delivery of the compositions of the present invention including, but not limited to, embodiments, orally, parenterally, topically, and intravenously. In still further embodiments, the composition comprises a transdermal patch.

Compositions and method of the present invention find use in the therapeutic and/or prophylactic treatment of a variety of inflammatory bowel diseases.

In a preferred embodiment, the subject possesses symptoms of inflammatory bowel disease. In some embodiments, the subject is suffering from Crohn's disease. In other embodiments, the subject is suffering from ulcerative colitis. In still further embodiments, the subject is suffering from irritable bowel syndrome, celiac disease, stomach ulcers, diverticulitis, pouchitis, proctitis, mucositis, radiation-associated enteritis, short bowel disease, or chronic diarrhea. In a preferred embodiment, the administration of a composition comprising an angiotensin converting enzyme inhibitor and polyethylene glycol reduces the symptoms of disease (e.g. reduces the symptoms of inflammatory bowel disease, Crohn's disease, ulcerative colitis, irritable bowel syndrome, celiac disease, stomach ulcers, diverticulitis, pouchitis, proctitis, or chronic diarrhea). In some embodiments, the composition comprising an angiotensin converting enzyme inhibitor and polyethylene glycol is administered under conditions such that the symptoms of inflammatory bowel disease are reduced. In other embodiments, the subject is at risk for inflammatory bowel disease, and the therapeutic composition is administered prophylactically. In still further embodiments, a therapeutically effective amount of a composition comprising an angiotensin converting enzyme inhibitor and polyethylene glycol is administered to the subject. In some embodiments, the composition comprising an angiotensin converting enzyme inhibitor and polyethylene glycol is administered in conjunction with one or more other therapeutic compounds (e.g., known therapeutic compounds such as steroids; for example, at a lower dose than if given without our compound). In some preferred embodiments, the composition comprising an angiotensin converting enzyme inhibitor and polyethylene glycol is co-administered with a corticosteroid. In some embodiments, the corticosteroid is prednisone.

It is not intended that the present invention be limited to a particular ACE inhibitor. Indeed, a variety of ACE inhibitors are contemplated including, but not limited to, alacepril, benazepril, captopril, cilazapril, ceranapril, delapril, enalapril, enalaprilat, fosinopril, fosinoprilat, imidapril, lisinopril, moexipril, perindopril, perindoprilat, quinapril, quinaprilat, ramipril, saralasin acetate, spirapril, temocapril, trandolapril, fasidotrilat, beclometasone dipropionate, FPL-66564, idrapril, MDL-100240, and S-5590.

The present invention also provides a method of treatment, comprising, providing a subject at risk for inflammatory bowel disease or other non-inflammatory gastrointestinal disorders (e.g., short bowel syndrome) and a composition comprising an angiotensin converting enzyme inhibitor and polyethylene glycol, and administering to the subject a therapeutically effective amount of the composition so as to prevent the subject from experiencing symptoms of inflammatory bowel disease, related inflammatory conditions of the gastrointestinal tracts, or other gastrointestinal disorders. In a preferred embodiment, the administration of the therapeutic composition comprising an angiotensin converting enzyme inhibitor and polyethylene glycol delays the progression of the symptoms of inflammatory bowel disease. In one embodiment, the subject at risk for inflammatory bowel disease is a human. In a preferred embodiment, the human is selected from a young adult, a person living in the United States, a person living in England, a person living in Northern Europe, a person of Jewish descent, a person living in a developing nation, a person with family members who suffer from inflammatory bowel disease or a person determined to carry an inflammatory bowel disease risk gene. In a particularly preferred embodiment, the administration of the therapeutic composition comprising an angiotensin converting enzyme inhibitor and polyethylene glycol prevents the onset of one or more symptoms of inflammatory bowel disease (e.g. prevents the onset of abdominal pain, diarrhea, rectal bleeding, weight loss, fever, loss of appetite, dehydration, anemia, or malnutrition, or any combination thereof).

In some embodiments, the composition is administered orally to the subject at risk for inflammatory bowel disease. In other embodiments, the composition is administered to the subject parenterally, topically, or intravenously. In still further embodiments, the composition comprises a transdermal patch. In some preferred embodiments, the composition comprising an angiotensin converting enzyme inhibitor and polyethylene glycol is administered rectally (e.g., via an enema).

In some embodiments, the subject at risk for developing gastrointestinal inflammation or inflammatory bowel disease is at risk for developing Crohn's disease, irritable bowel syndrome, celiac disease, ulcerative colitis, stomach ulcers, diverticulitis, pouchitis, proctitis, mucositis, radiation-induced enteritis or chronic diarrhea.

In some embodiments, the compositions of the invention are administered to infants, children, and adults who suffer from short bowel syndrome. In this condition, the subject is lacking a sufficient length of the gastrointestinal tract to permit the normal absorption of fluids, electrolytes and nutrients to permit growth and survival. In such a condition, the subject requires supplementation with either specialized enteral or parenteral nutrients. The use of a composition comprising an angiotensin converting enzyme inhibitor and polyethylene glycol, in some embodiments of the present invention, is administered to such individuals to facilitate growth and adaptation of the gastrointestinal tract. In such embodiments, the compositions of the present invention are used to treat or improve the disorder of short bowel syndrome, although an understanding of the mechanism is not necessary to practice the present invention and the invention is not limited to any particular mechanism of action.

In some preferred embodiments, the composition comprising an angiotensin converting enzyme inhibitor and polyethylene glycol is administered rectally (e.g., via an enema) to a subject at risk for short bowel syndrome. In other embodiments, the compositions are administered to the subject parenterally, topically, intravenously, or orally. In still further embodiments, the composition comprises a transdermal patch.

DEFINITIONS

Figure 1:
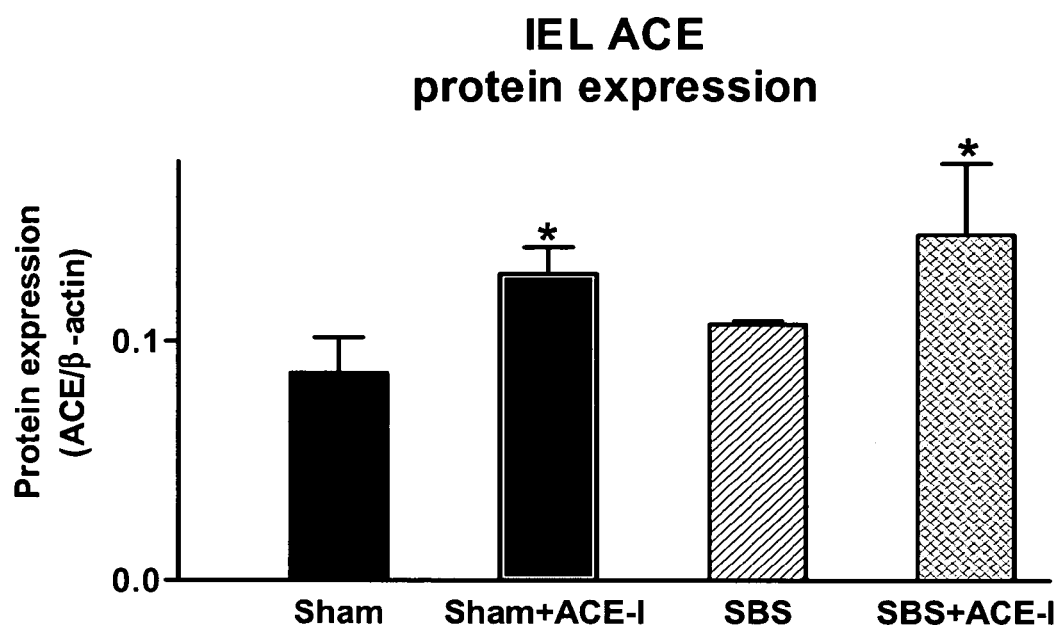
FIG. 1 depicts intraepithelial lymphocyte ACE protein expression in Sham mice, mice after massive small bowel resection, and mice with massive small bowel resection administered ACE inhibitors.

To facilitate an understanding of the present invention, a number of terms and phrases are defined below:

"Gastrointestinal inflammation" as used herein refers to inflammation of a mucosal layer of the gastrointestinal tract, and encompasses acute and chronic inflammatory conditions. Acute inflammation is generally characterized by a short time of onset and infiltration or influx of neutrophils. Chronic inflammation is generally characterized by a relatively longer period of onset and infiltration or influx of mononuclear cells. Chronic inflammation can also typically characterized by periods of spontaneous remission and spontaneous occurrence. "Mucosal layer of the gastrointestinal tract" is meant to include mucosa of the bowel (including the small intestine and large intestine), rectum, stomach (gastric) lining, oral cavity, and the like.

"Chronic gastrointestinal inflammation" refers to inflammation of the mucosal of the gastrointestinal tract that is characterized by a relatively longer period of onset, is long-lasting (e.g., from several days, weeks, months, or years and up to the life of the subject), and is associated with infiltration or influx of mononuclear cells and can be further associated with periods of spontaneous remission and spontaneous occurrence. Thus, subjects with chronic gastrointestinal inflammation may be expected to require a long period of supervision, observation, or care. "Chronic gastrointestinal inflammatory conditions" (also referred to as "chronic gastrointestinal inflammatory diseases") having such chronic inflammation include, but are not necessarily limited to, inflammatory bowel disease (IBD), colitis induced by environmental insults (e.g., gastrointestinal inflammation (e.g., colitis) caused by or associated with (e.g., as a side effect) a therapeutic regimen, such as administration of chemotherapy, radiation therapy, and the like), colitis in conditions such as chronic granulomatous disease (Schappi et al., Arch. Dis. Child., 1984:147 (2001)), celiac disease, celiac sprue (a heritable disease in which the intestinal lining is inflamed in response to the ingestion of a protein known as gluten), food allergies, gastritis, infectious gastritis or enterocolitis (e.g., Helicobacter pylori-infected chronic active gastritis) and other forms of gastrointestinal inflammation caused by an infectious agent, and other like conditions.

The acute and chronic inflammation is secondary to an increase in pro-inflammatory cytokines (particularly tumor necrosis factor-alpha) and an increase in epithelial cell apoptosis. The resultant manifestations of these factors are a loss of the mucosal epithelial lining and the above stated neutrophil/monocyte infiltrate.

As used herein, "inflammatory bowel disease" or "IBD" refers to any of a variety of diseases characterized by inflammation of all or part of the intestines. Examples of inflammatory bowel disease include, but are not limited to, Crohn's disease, ulcerative colitis, irritable bowel syndrome, mucositis, radiation induced enteritis, short bowel syndrome, celiac disease, colitis, stomach ulcers, diverticulitis, pouchitis, proctitis, and chronic diarrhea. Reference to IBD throughout the specification is often referred to in the specification as exemplary of gastrointestinal inflammatory conditions, and is not meant to be limiting.

As used herein, the term "symptoms of IBD" is herein defined to detected symptoms such as abdominal pain, diarrhea, rectal bleeding, weight loss, fever, loss of appetite, and other more serious complications, such as dehydration, anemia and malnutrition. A number of such symptoms are subject to quantitative analysis (e.g. weight loss, fever, anemia, etc.). Some symptoms are readily determined from a blood test (e.g. anemia) or a test that detects the presence of blood (e.g. rectal bleeding). The term "wherein said symptoms are reduced" refers to a qualitative or quantitative reduction in detectable symptoms, including but not limited to a detectable impact on the rate of recovery from disease (e.g. rate of weight gain). The diagnosis is typically determined by way of an endoscopic observation of the mucosa, and pathologic examination of endoscopic biopsy specimens.

As used herein, the term "a therapeutically effective amount" of a composition comprising ACE inhibitors is herein defined as the dosage level required for a subject such that the subject's symptoms of IBD are reduced.

As used herein, the phrase "under conditions such that the symptoms are reduced" refers to any degree of qualitative or quantitative reduction in detectable symptoms of IBD, including but not limited to, a detectable impact on the rate of recovery from disease (e.g. rate of weight gain), or the reduction of at least one of the following symptoms: abdominal pain, diarrhea, rectal bleeding, weight loss, fever, loss of appetite, dehydration, anemia, distention, fibrosis, inflamed intestines and malnutrition.

As used herein, the term "at risk for IBD" is herein defined as encompassing the segment of the world population that has an increased risk (i.e. over the average person) for IBD and can occur at any age. It occurs worldwide, but is most common in the United States, England, and northern Europe. It is especially common in people of Jewish descent. An increased frequency of this condition has been recently observed in developing nations. Increased risk is also most prevalent in people with family members who suffer from inflammatory bowel disease.

As used herein, the term "therapeutic composition comprising ACE inhibitors" refers to compositions containing ACE inhibitors together with one or more other compounds or agents including, but not limited to, other ACE inhibitors, other therapeutic agents, physiologically tolerable liquids, gels, carriers, diluents, adjuvants, excipients, salicylates, steroids, immunosuppressants, antibodies, cytokines, antibiotics, binders, fillers, preservatives, stabilizing agents, emulsifiers, and buffers.

As used herein, the term "continuous manner" when used in reference to the method of delivery or administration of the therapeutic composition comprising ACE inhibitors of the present invention is defined as meaning a substantially uninterrupted administration such that a therapeutic dosage is stretched over a period of time and avoids dosage spiking that is common among other modes of administration (e.g. oral administration or intravenous administration). Examples of modes of administration that employ a continuous manner of delivery include, but are not limited to, a transdermal patch, a suppository, or a slow release oral formulation. As used herein, the term "subject" refers to a patient that is administered the therapeutic composition comprising ACE inhibitors of the present invention. Examples of subjects, include, but are not limited to, humans and other mammals such as non-human primates, horses, dogs, and cats.

As used herein, the terms "host," "subject" and "patient" refer to any animal, including but not limited to, human and non-human animals (e.g. rodents, arthropods, insects (e.g., Diptera), fish (e.g., zebrafish), non-human primates, ovines, bovines, ruminants, lagomorphs, porcines, caprines, equines, canines, felines, aves, etc.), that is studied, analyzed, tested, diagnosed or treated. As used herein, the terms "host," "subject" and "patient" are used interchangeably.

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "effective amount" refers to the amount of a composition (e.g., comprising a an ACE inhibitor) sufficient to effect beneficial or desired results. An effective amount can be administered in one or more administrations, applications or dosages and is not intended to be limited to a particular formulation or administration route.

As used herein, the terms "administration" and "administering" refer to the act of giving a drug, prodrug, or other agent, or therapeutic treatment (e.g., compositions of the present invention) to a subject (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, rectal, by injection (e.g., intravenously, subcutaneously, intratumorally, intraperitoneally, etc.) and the like.

As used herein, the terms "co-administration" and "co-administering" refer to the administration of at least two agent(s) (e.g., composition comprising an ACE inhibitor and one or more other agents—e.g., a steroid) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "treatment" or grammatical equivalents encompasses the improvement and/or reversal of the symptoms of disease (e.g., inflammatory bowel disease). A compound which causes an improvement in any parameter associated with disease when used in the screening methods of the instant invention may thereby be identified as a therapeutic compound. The term "treatment" refers to both therapeutic treatment and prophylactic or preventative measures. For example, those who may benefit from treatment with compositions and methods of the present invention include those already with a disease and/or disorder (e.g., inflammatory bowel disease) as well as those in which a disease and/or disorder is to be prevented (e.g., using a prophylactic treatment of the present invention).

As used herein, the term "at risk for disease" refers to a subject (e.g., a human) that is predisposed to experiencing a particular disease. This predisposition may be genetic (e.g., a particular genetic tendency to experience the disease, such as heritable disorders), or due to other factors (e.g., environmental conditions, exposures to detrimental compounds present in the environment, etc.). Thus, it is not intended that the present invention be limited to any particular risk, nor is it intended that the present invention be limited to any particular disease.

As used herein, the term "suffering from disease" refers to a subject (e.g., a human) that is experiencing a particular disease. It is not intended that the present invention be limited to any particular signs or symptoms, nor disease. Thus, it is intended that the present invention encompass subjects that are experiencing any range of disease (e.g., from sub-clinical manifestation to full-blown disease) wherein the subject exhibits at least some of the indicia (e.g., signs and symptoms) associated with the particular disease.

As used herein, the terms "disease" and "pathological condition" are used interchangeably to describe a state, signs, and/or symptoms that are associated with any impairment of the normal state of a living animal or of any of its organs or tissues that interrupts or modifies the performance of normal functions, and may be a response to environmental factors (such as malnutrition, industrial hazards, or climate), to specific infective agents (such as worms, bacteria, or viruses), to inherent defect of the organism (such as various genetic anomalies, or to combinations of these and other factors.

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present invention. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of disease (e.g., inflammatory bowel disease).

"Short Bowel Syndrome" refers to the condition of the gastrointestinal tract whereby the bowel is lacks an adequate length to allow for the sufficient length to absorb nutrients, fluids and/or electrolytes.

"Intestinal Failure" refers to the condition of a gastrointestinal tract which lacks sufficient ability to absorb nutrients, fluids and electrolytes to sustain an organism, and to provide for growth. The condition includes, but is not limited, to conditions of short bowel syndrome, malabsorption, overwhelming inflammatory conditions of the bowel, and dymotility syndromes (conditions whereby the bowel lacks adequate mobility to propel nutrients through the intestine).

DETAILED DESCRIPTION OF THE INVENTION

The present invention provides compositions and methods for treating and preventing inflammatory bowel disease and related conditions. In addition, the present invention provides compositions and methods for the treatment of short bowel syndrome (SBS) and other related problems of intestinal failure. In particular, the present invention provides methods of treating symptoms of inflammatory bowel disease, short bowel syndrome, intestinal failure and related conditions using a composition comprising an angiotensin converting enzyme (ACE) inhibitor (e.g., Enalaprilat) and polyethylene glycol (e.g., of 1000 molecular weight).

Experiments conducted during the development of the present invention demonstrated that the ACE inhibitors find use in the treatment and prevention of gastrointestinal inflammation diseases and conditions, including inflammatory bowel disease (See Examples 2-8). Additional experiments demonstrate that use of ACE inhibitors may be effective in improving intestinal adaptation in cases of the short bowel syndrome, and may be used as a therapeutic modality in such conditions. Thus, the present invention provides new compositions and methods for using ACE inhibitors in the treatment and prevention of such conditions. The ACE inhibitors of the present invention may be used alone, or in combination with any other known or later identified treatment or intervention for such gastrointestinal inflammation diseases and short bowel syndrome conditions.

Examples of ACE inhibitors that find use in the compositions and methods of the present invention include, but are not limited to, Beecham's BRL 36,378 as disclosed in European patent Nos. 80822 and 60668; Chugai's MC-838 disclosed in CA. 102:72588v and Jap. J. Pharmacol. 40:373 (1986); Ciba-Geigy's CGS 14824 (3-([1-ethoxycarbonyl-3-phenyl-(1S)-propyl]-amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechst) disclosed in Eur. Patent No. 79-022 and Curr. Ther. Res. 40:74 (1986); Ru 44570 (Hoechst) disclosed in Arzneimittelforschung 35:1254 (1985), cilazapril (Hoffman-LaRoche) disclosed in J. Cardiovasc. Pharmacol. 9:39 (1987); R.sub.O 31-2201 (Hoffman-LaRoche) disclosed in FEBS Lett. 165:201 (1984); lisinopril (Merck) disclosed in Curr. Therap. Res. 37:342 (1985) and Eur. patent appl. No. 12-401, indalapril (delapril) disclosed in U.S. Pat. No. 4,385,051; rentiapril (fentiapril, Santen) disclosed in Clin. Exp. Pharmacol. Physiol. 10:131 (1983); indolapril (Schering) disclosed in J. Cardiovasc. Pharmacol. 5:643, 655 (1983); spirapril (Schering) disclosed in Acta. Pharmacol. Toxicol. 59 (Supp. 5):173 (1986); perindopril (Servier) disclosed in Eur. J. Clin. Pharmacol. 31:519 (1987); quinapril (Warner-Lambert) disclosed in U.S. Pat. No. 4,344, 949 and CI 925 (Warner-Lambert) ([3S-[2[R(*)R(*)]]3R (*)]-2-[2-[[1-(ethoxy-carbonyl)-3-phenylpropyl]amino[-1-oxopropyl]-1,2,3,4-tetrahydro-6,7-dimethoxy-3-isoquinolinecarboxylic acid HCl) disclosed in Pharmacologist 26:243, 266 (1984), WY-44221 (Wyeth) disclosed in J. Med. Chem. 26:394 (1983), each of which is hereby incorporated by reference in its entirety.

In preferred embodiments, the present invention provides a composition comprising an ACE inhibitor (e.g., Enalaprilat) and polyethylene glycol (e.g., of 1000 molecular weight). In further preferred embodiments, the ACE inhibitor is suspended in the relatively non-inert polyethylene glycol carrier (e.g., 1000 molecular weight). This compound can be directly delivered to a subject (e.g., via rectal or oral administration). Additionally, in some embodiments, the composition comprising an ACE inhibitor and polyethylene glycol may comprise one or more other agents (e.g., a steroid such as prednisone). Thus, in some embodiments, direct administration to a subject rectally via an enema circumvents systemic immunosuppression accompanied with systemic administration of steroids.

Although an understanding of the mechanism is not necessary to practice the present invention and the present invention is not limited to any particular mechanism of action, a composition comprising polyethylene glycol and an ACE inhibitor provides semi-selective absorption of the composition (e.g., although polyethylene glycol (1000 molecular weight) is generally non-absorbable in mucosa that is non-inflamed and intact, it can pass into the intestinal wall exhibiting inflammation and ulcerations that are present during a state of active inflammation, thereby providing the composition directly to areas that may benefit from a maximal amount of therapy). This semi-selective targeting can also be used in the selection of an enteral administration of the ACE-inhibitor, as ACE is expressed in the intestine is along the epithelial cell lining of the lumen of the gut. Furthermore, certain types of ACE-inhibitors can be selected for use in the compositions and methods of the present invention, based on their inability to be absorbed by healthy mucosa, thereby providing increased specificity of the compositions and methods. For example, enalaprilat can be selected as the ACE inhibitor because it is not normally absorbed through mucosa which is non-inflamed and intact. Thus, in preferred embodiments, the composition comprising polyethylene glycol and an ACE inhibitor is administered directly onto the inflamed mucosal lining (e.g., it is not administered systemically). However, in some embodiments, a composition comprising polyethylene glycol and an ACE inhibitor is modified to be given orally.

Compositions and methods of the present invention provide a minimal systemic immunosuppressive effect: Specifically, the direct administration of this agent to the gastrointestinal tract avoids many of the adverse systemic effects of current agents. For example, one of the advantages in the use of an ACE inhibitor, in general, for the treatment of inflammatory bowel disease is that this agent lacks systemic immunosuppressive properties, properties that are inherent in medicines currently used for this inflammatory bowel disease (e.g., steroids).

The present invention further provides a method of treating a subject with inflammatory bowel disease comprising administering to the subject a composition comprising polyethylene glycol and an ACE inhibitor, and co-administrating one or more steroids (e.g., prednisone). In some preferred embodiments, co-administration of these compositions reduces the dose of steroid (e.g., prednisone) required to provide a beneficial effect (e.g., the dose of steroid is lower than in conventional treatments using the steroid independently).

Treatment of the various intestinal bowel diseases and disorders described herein are often generally limited by the following two major factors: (1) the development of drug resistance and (2) the toxicity of known therapeutic agents (e.g., systemic immunosuppression associated with systemic administration of steroids). Some therapeutic agents have deleterious side effects, including non-specific lymphotoxicity and renal toxicity.

The methods described herein address both these problems. Drug resistance, where increasing dosages are required to achieve therapeutic benefit, is overcome by co-administering the compounds comprising polyethylene glycol and an ACE inhibitor described herein with the known agent (e.g., steroid). In some embodiments, the compounds described herein sensitize target cells (e.g., colonic mucosal epithelial cells) to known agents (and vice versa) and, accordingly, less of these agents (e.g., steroids) are needed to achieve a therapeutic benefit.

The sensitizing function of the claimed compounds also addresses the problems associated with toxic effects of known therapeutics. In instances where the known agent is toxic, it is desirable to limit the dosages administered in all cases, and particularly in those cases where drug resistance has increased the requisite dosage. Thus, in some embodiments, when the claimed compounds are co-administered with the known agent, they reduce the dosage required which, in turn, reduces the deleterious effects. Further, because the claimed compounds are themselves both effective and non-toxic in moderate doses, co-administration of proportionally more of these compounds than known toxic therapeutics will achieve the desired effects while minimizing toxic effects.

Thus, in general, co-administration of a compound comprising polyethylene glycol and an ACE inhibitor with a steroid has the advantage of less systemic immunosuppressive action on the patient (for example, due to the ability of administering lower doses of the steroid in combination with compositions and methods of the present invention (e.g., compared to the level of steroid required to provide the same effect in the absence of a composition of the present invention)).

ACE inhibitors inhibit the expression of tumor necrosis factor-alpha (TNF-α) and alters growth and survival of colonic mucosal epithelial cells. TNF-α is known to be markedly up-regulated in inflammatory bowel disease conditions (e.g., including Crohn's disease and ulcerative colitis). Second, TNF-α alters growth and survival characteristics of colonic mucosal epithelial cells. A major mechanism in colitic conditions is an increase in epithelial cell death (apoptosis). Thus, although an understanding of the mechanism is not necessary to practice the present invention and the present invention is not limited to any particular mechanism of action, administration of a compound comprising polyethylene glycol and an ACE inhibitor markedly decreases the rate of epithelial cell apoptosis and/or increases the rate of epithelial cell proliferation. A combined effect of these actions on the mucosal surface is to allow for healing of the injured colonic lining (e.g., improving the histologic appearance during a colitic episode). The present invention also provides the ability to coat the gastrointestinal mucosal lining. Use of a composition comprising polyethylene glycol (PEG 1000) and an ACE inhibitor (e.g., enalaprilat) provides for the delivery of the ACE inhibitor with a non-irritating, relatively inert, non-toxic agent (e.g., polyethylene glycol; See Example 9). A number of different forms of polyethylene glycol are contemplated to be useful in the present invention including, but not limited to, 200, 300, 400, 600, 1000, 1450, 3350, 4000, 6000, 8000 and 20000 molecular weight polyethylene glycol. Polyethylene glycol used in the present invention may be linear or branched. Although an understanding of the mechanism is not necessary to practice the present invention and the present invention is not limited to any particular mechanism of action, administration of compositions of the present invention with an enema, because polyethylene glycol has viscous consistency, permits the composition comprising polyethylene glycol and an ACE inhibitor to thoroughly coat the colonic wall (e.g., prevents it from falling away from the wall with peristalsis or gravity). In some embodiments, the longer the composition comprising polyethylene glycol and an ACE inhibitor are in contact with inflamed colonic mucosal tissue, the greater the beneficial effect provided to a subject. In some embodiments, a composition comprising polyethylene glycol and an ACE inhibitor are used for oral administration for coating and action on inflamed tissues of the oral cavity, esophagus, stomach and small intestine.

The present invention provides pharmaceutical compositions which may comprise polyethylene glycol and an ACE inhibitor, alone, or in combination with at least one other agent, such as a stabilizing compound, or a steroid (e.g., prednisone), and may be administered in any sterile, biocompatible pharmaceutical carrier, including, but not limited to, saline, buffered saline, dextrose, and water.

The methods of the present invention find use in treating (e.g., prophylacticly or therapeutically) diseases or altering physiological states. A composition comprising polyethylene glycol and an ACE inhibitor can be administered to a subject (e.g., a patient) intravenously in a pharmaceutically acceptable carrier such as physiological saline. Standard methods for intracellular delivery of compounds can be used (e.g., delivery via liposome). Such methods are well known to those of ordinary skill in the art. The formulations of this invention are useful for parenteral administration, such as intravenous, subcutaneous, intramuscular, and intraperitoneal.

As is well known in the medical arts, dosages for any one subject may depend upon many factors, including the patient's size, body surface area, age, the particular compound to be administered, sex, time and route of administration, general health, and interaction with other drugs being concurrently administered.

Accordingly, in some embodiments of the present invention, compositions and/or formulations comprising polyethylene glycol and an ACE inhibitor can be administered to a subject alone, or in combination with other drugs, small molecules, or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, compositions comprising polyethylene glycol and an ACE inhibitor may be administered alone to individuals subject to or suffering from a disease or condition (e.g., inflammatory bowel disease).

These pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; rectal administration, as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of the pharmaceutical agent may be that amount that reduces inflammation associated with inflammatory bowel disease or alters the expression of a TNF-α. Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations which can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Thus, for oral administration, a satisfactory result may be obtained employing the ACE inhibitor in an amount within the range of from about 0.01 mg/kg to about 100 mg/kg and preferably from about 0.1 mg/kg to about 25 mg/kg, and when employing ceronapril preferably from about 0.01 to about 10 mg/kg, alone or in combination with other drugs in an amount within the range of from about 0.01 mg/kg to about 100 mg/kg and preferably from about 0.1 mg/kg to about 25 mg/kg with the ACE inhibitor and other drugs being employed together in the same oral dosage form or in separate oral dosage forms taken at the same time.

A preferred oral dosage form, such as tablets or capsules, will contain the ACE inhibitor in an amount of from about 1 to about 500 mg, preferably from about 125 to about 200 mg, and more preferably from about 25 to about 150 mg.

For parenteral administration, the ACE inhibitor will be employed in an amount within the range of from about 0.001 mg/kg to about 10 mg/kg and preferably from about 0.01 mg/kg to about 1 mg/kg.

In some preferred embodiments, a composition comprising an ACE inhibitor and polyethylene glycol (e.g., PEG 1000) is administered to a subject via an enema. The present invention is not limited by the amount or type of ACE inhibitor used for administration via enema. In some embodiments, an enema will contain from about 0.0001 mg/kg to about 10 mg/kg of the ACE inhibitor per kilogram weight of the subject administered the enema, although lower and higher concentrations are contemplated. In some embodiments, an enema will contain between 0.1 and 1 µg of the ACE inhibitor per kilogram weight of the subject administered the enema. In some embodiments, an enema will contain between 1.0 and 10 µg of the ACE inhibitor per kilogram weight of the subject administered the enema. In some embodiments, an enema will contain between 10 and 100 μg of the ACE inhibitor per kilogram weight of the subject administered the enema. In some embodiments, an enema will contain between 100 μg and 1 mg of the ACE inhibitor per kilogram weight of the subject administered the enema. In some embodiments, an enema will contain between 1 mg and 10 mg of the ACE inhibitor per kilogram weight of the subject administered the enema. In some embodiments, an enema will contain more than 10 mg of the ACE inhibitor per kilogram weight of the subject administered the enema. In some embodiments, an enema is administered to a subject once daily. In some embodiments, an enema is administered to a subject twice daily. In some embodiments, an enema is administered to a subject three or more times a day. In some embodiments, an enema is administered to a subject one, two, three or more times a week. In some preferred embodiments, the ACE inhibitor administered to a subject via an enema is enalaprilat. In some embodiments, the ACE inhibitor administered to a subject via an enema is any one or more of the ACE inhibitors described herein.

The composition described above may be administered in the dosage forms as described above in single or divided doses of one to multiple times daily, or continuously or semi-continuously (See e.g., U.S. Pat. No. 6,267,990 for controlled release techniques, herein incorporated by reference in its entirety).

Compositions comprising a compound of the invention formulated in a pharmaceutical acceptable carrier may be prepared, placed in an appropriate container, and labeled for treatment of an indicated condition. For compositions or formulations comprising polyethylene glycol and an ACE inhibitor, conditions indicated on the label may include treatment of condition related to prophylactic or therapeutic treatment of inflammatory bowel disease.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the methods of the invention, the therapeutically effective dose can be estimated initially from cell culture assays. Then, preferably, dosage can be formulated in animal models (particularly murine models) to achieve a desirable circulating concentration range.

A therapeutically effective dose refers to that amount of which ameliorates or prevents symptoms of a disease state or condition. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds which exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage may be chosen by a subject's physician in view of the patient to be treated. Dosage and administration are adjusted to provide sufficient levels of the active moiety or to maintain the desired effect (e.g., reduction of inflammatory colonic tissue). Additional factors that may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. As described above, compositions and formulations comprising polyethylene glycol and an ACE inhibitor are believed to be particularly useful for rectal administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

In some embodiments, the invention provide pharmaceutical compositions containing (a) polyethylene glycol and an ACE inhibitor, and (b) one or more other agents (e.g., a steroid). Examples of steroids include, but are not limited to, cortisol, prednisone and other corticosteroids. In some embodiments, two or more combined agents (e.g., steroids) may be used together or sequentially.

The present invention also includes methods involving co-administration of compounds comprising polyethylene glycol and an ACE inhibitor described herein with one or more additional active agents (e.g., a corticosteroid.). Indeed, it is a further aspect of this invention to provide methods for enhancing prior art therapies and/or pharmaceutical compositions by co-administering a composition comprising polyethylene glycol and an ACE inhibitor of this invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered agents may each be administered using different modes or different formulations.

The agent or agents to be co-administered depends on the type of condition being treated. For example, when the condition being treated is an inflammatory bowel disease, the additional agent can be a corticosteroid, or other type of immunosuppressive agent. The additional agents to be co-administered, such as immunosuppressive agents or corticosteroids can be any of the well-known agents in the art, including, but not limited to, those that are currently in clinical use.

EXPERIMENTAL

The following examples are provided in order to demonstrate and further illustrate certain preferred embodiments and aspects of the present invention and are not to be construed as limiting the scope thereof.

Example 1

Materials and Methods

Animals: Male, 2 month old, C57BL/6J mice (Jackson Laboratories, Bar Harbor, Me.) were maintained in a 12-hour day-night rhythm at 23° C. and a relative humidity of 40%-60%. 24 hours before surgery chow was exchanged to microstabilized rodent liquid diet (TestDiet, Richmond, Ind.). Anesthesia was achieved using sodium pentobarbital (50 mg/kg body weight, intraperitoneally, i.p.). For some experiments B6.129P2-Ace$^{tm2Unc}$ (ACE$^{-/-}$; lacking somatic ACE, generous gift from the Dr. O. Smithies, Duke University), or B6;129S6-Tnf$^{tm1Gkl}$ (TNF-α-knockout mice, Jackson Labs) were used. Studies conformed, and were approved by the University Committee on Use and Care of Animals at the University of Michigan.

Short Bowel Syndrome Model: A 70% mid-small bowel resection was performed (i.e. bowel between 3.5 cm distal to the ligament of Treitz and 3.5 cm proximal to the ileocecal valve), followed by an end-to-end jejuno-ileal anastomosis with 7-0 monofilament, absorbable suture. Postoperatively a subcutaneous bolus of 3 ml 0.9% saline solution was given to maintain hydration status.

Sham operation: Mid-small bowel was transsected and re-anastomosed without bowel-resection.

Post-Surgery: Postoperatively ad libitum water and liquid diet were reintroduced. If mice were not sacrificed after 10 days, food was changed to standard chow. Four groups were studied (N=6 per group): 1 week (SBR 1 w, Sham 1 w) or 4 weeks (SBR 4 w, Sham 4 w), to assess temporal changes. Animals were sacrificed using $CO_2$, and the intestine was harvested.

Histology: A 0.5 cm segment of mid-small bowel was fixed in 10% formaldehyde, and processed for hematoxylin and eosin staining. Villus height and crypt depth were measured using a calibrated micrometer. Each measurement consisted of a mean of 16 different low power fields.

Epithelial cell apoptosis assays: Two methods were used to assess EC apoptosis.

Annexin V staining: Apoptosis was determined by flow cytometry based on the cell surface expression of phosphatidylserine using Annexin V staining (BD PharMingen, San Diego, Calif.). Propidium iodide was utilized to simultaneously monitor cell necrosis. Flow cytometry was performed by using standard techniques. Separation of EC from IEL was done by forward- and side-scatter gating characteristics. Further confirmation of EC and IEL purity was performed with specific staining of EC with antibody generated by a hybridoma G8.8 and a panlymphoid antibody (anti-CD45, PharMingen, San Diego, Calif.): Purity exceeded >98%.

TUNEL staining: Paraffin-embedded tissue was assayed with TUNEL (Terminal deoxynucleotidyl transferase Biotin-dUTP Nick End Labeling) staining, according to slight modification of manufacturer's instructions (ApopTag InSitu Apoptosis Detection Kit, Serological Corporation, Norcross, Ga.): slides were incubated with only ⅓ of the recommended concentration of TdT enzyme, in order to avoid over-staining. Apoptosis rate (percent of EC showing apoptosis) was assessed with TUNEL staining and by morphological criteria (nuclear margination, chromatin and cytoplasmic condensation, shrinkage from neighboring cells, and formation of apoptotic bodies with nuclear and cytoplasmic fragmentation). Each assessment of apoptosis consists of the mean of 8 different crypt-villus-complexes.

Mucosal cell isolation: Isolation of mucosal cells was performed using standard protocols. This included isolation of cells with an extraction buffer (1 mM EDTA, 1 mM dithiotheritol in phosphate buffer saline), and purification in 20% isotonic Percoll (Pharmacia, Piscataway, N.J.). Viability exceeded 95% using trypan blue exclusion staining. The cell suspension contained a purified mixture of EC and IEL at a ratio of 60:40.

IEL purification: Isolation of purified IEL from EC was performed by direct magnetic separation. Magnetic beads conjugated with antibody to CD45 (pan-lymphoid marker) were used to segregate IEL from EC (BioMag SelectaPure Anti-Mouse CD 45R Antibody Particles, Polyscience Inc., Warrington, Pa.). Magnetic separation was performed twice to further deplete EC. Final IEL purity was greater than 99% by flow cytometry.

IEL staining and sorting: IEL were stained with antibodies to T-cell receptor (TCR)-αβ (H57, Invitrogen Corporation, Gibco BRL, Carlsbad, Calif.), TCR-γδ (GL3, Invitrogen), CD4 (RM4-5, BD PharMingen, San Diego, Calif.) or CD8α (53-6.7, PharMingen). Isotype control antibodies were used to adjust gating. IEL sub-populations were sorted using an EPICS Elite (Coulter, Miami, Fla.) flow cytometer. Sorted IEL were kept at 4° C. until RNA isolation.

Isolation of total RNA: A guanidine isothiocyanate/chloroform extraction method was performed using Trizol (Gibco BRL, Gaithersburg, Md.) according to manufacturer's directions.

Microarray assay: Total IEL-RNA was purified with the RNeasy Mini Kit (Qiagen, Valencia, Calif.). Affymetrix system microarray chips (U74 set, Affymetrix, Inc., Santa Clara, Calif.) allowed simultaneous interrogation of 12,491 full-length mouse genes and EST clusters from the UniGene database. Hybridization and analysis were performed by the University of Michigan NIDDK Biotechnology Center. Probe-pair measures were obtained from the images of each chip using Microarray Suite 4.0 software (Affymetrix).

Reverse transcriptase polymerase chain reaction (RT-PCR): mRNA (poly-A positive) was reversed transcribed into cDNA following a standard protocol. Specific primers for selected gene sequences were designed. PCR and gel were run under standard conditions. To ensure that DNA product was generated at the exponential portion of the product curve, the following cycle numbers were used: 28 cycles for ACE; 32 cycles for Rap2 interacting protein and TNF-α; and 34 cycles for lipocalin 2, amphiregulin, leucine-rich-α2-glycoprotein, and angiotensin II receptors. Gel bands were analyzed by DNA sequencing to ensure the correct product. Kodak EDAS System (Rochester, N.Y.) was used for imaging and quantification. Results were expressed as the ratio of the investigated mRNA over the β-actin mRNA expression.

Real time PCR: Real-time PCR was run to better quantify actual changes in ACE expression. cDNA was also used for real time PCR. The same primers for ACE and β-actin were used as for conventional PCR, SYBR Green I was utilized for fluorescence. PCR was run with the following steps: 94° C. for 15 seconds, 66° C. for 15 seconds, and 72° C. for 25 seconds. A cDNA standard curve was created with defined concentrations of cDNA. This allowed for an extrapolation of the numbers of copies using the following formula: cDNA copies/ml=DNA concentration (mg/ml)×($10^6$ pg/mg)×(pmol/660 pg)×(1/sequence size [bp])×($10^{12}$ mol/$10^3$ ml)×$6.023 \times 10^{23}$. Ct-values of ACE and β-actin were converted to numbers of cDNA copies, and results expressed as the ratio of ACE over β-actin expression.

Immunoblot analysis: Protein was extracted from isolated IEL and immunoblots performed by using a Bio-Rad protein assay kit (Bio-Rad Laboratories, Hercules, Calif.), with standard methods. Purified anti-ACE (Clone 3G8) (1:1000, Chemicon International, Temecula, Calif.) was used for ACE detection. Expression for β-actin was determined in the same fashion by re-probing membranes with purified anti-mouse β-actin (1:12000, Sigma-Aldrich, St. Louis, Mo.). Results are expressed as the ratio of ACE over β-actin protein expression.

Epithelial cell proliferation: Mice were given a dose of bromodeoxyuridine (BrdU) 1 to 2 hours prior to sacrifice. Tissues harvested from the intestine were subsequently stained for BrdU as a marker of cellular proliferation.

Statistical analysis: Microarray gene analysis was performed using ArrayAssist software (Iobion Corp.). Initial analysis incorporated raw chip data and compared all study groups matched by week of study. Statistics utilized a modification of the paired t-test comparison consisting of a Benjamini-Hochberg correction (RMA analysis). Data criteria was considered significant if fold-change (FC) between groups was >2 and P<0.05 (F-test), or FC>3 and 0.05>P>0.01, or FC>4 and P>0.05. Significantly elevated genes were then selected based on identified gene functions relating to either cell proliferation and/or apoptosis. Remaining data are expressed as mean±standard deviation. These results were analyzed using ANOVA with least significant difference for post-hoc testing; statistical significance was set at P<0.05.

Example 2

Microarray Analysis

Significant differential changes were noted in 65 genes at 1 week, and 254 genes after 4 weeks, between SBS and Sham groups. Genes were analyzed for relevance to proliferation or apoptosis. Five genes were identified (Table 1): angiotensin converting enzyme (ACE), lipocalin 2, Rap2 interacting protein, amphiregulin, and leucine-rich-α2-glycoprotein. Expression was confirmed for each with RT PCR. Although all five of these genes may have effects on EC growth, ACE was selected for additional examination due to its profound action on alveolar EC apoptosis.

TABLE 1

IEL-genes with greatest alterations in growth-modifying factors; shown are RT-PCR results expressed as the relative expression compared to β-actin (mean ± standard deviation, n = 6. †P < 0.05 Sham 1w vs. SBR 1w, *P < 0.05 Sham 4w vs. SBR 4w, ††P < 0.05 Sham 1w vs. Sham 4w, **P < 0.05 SBR 1w vs. SBR 4w

| Gene | Lipocalin 2 | Angiotensin converting enzyme | Rap2 interacting protein | Amphiregulin | Leucine-rich-α2-glycoprotein |
|---|---|---|---|---|---|
| Function | Apoptosis↑ | Apoptosis↑ | Apoptosis↓ Proliferation↑ | Proliferation↑ | Apoptosis↑ Proliferation↓ |
| Sham 1w mean | 0.72 ± 0.65†† | 0.93 ± 0.10† | 0.27 ± 0.17 | 0.31 ± 0.16 | 0.57 ± 0.28 |

TABLE 1-continued

IEL-genes with greatest alterations in growth-modifying factors; shown are RT-PCR results expressed as the relative expression compared to β-actin (mean ± standard deviation, n = 6. †P < 0.05 Sham 1w vs. SBR 1w, *P < 0.05 Sham 4w vs. SBR 4w, ††P < 0.05 Sham 1w vs. Sham 4w, **P < 0.05 SBR 1w vs. SBR 4w

| Gene | Lipocalin 2 | Angiotensin converting enzyme | Rap2 interacting protein | Amphiregulin | Leucine-rich-α2-glyco-protein |
|---|---|---|---|---|---|
| SBS 1w mean | 0.62 ± 0.13 | 1.04 ± 0.07 | 0.18 ± 0.13** | 0.18 ± 0.07** | 0.54 ± 0.11 |
| Sham 4w mean | 0.25 ± 0.22* | 0.89 ± 0.06†† | 0.26 ± 0.08 | 0.25 ± 0.09 | 0.34 ± 0.24* |
| SBS 4w mean | 0.45 ± 0.27 | 1.01 ± 0.24 | 0.21 ± 0.16 | 0.25 ± 0.11 | 0.47 ± 0.21 |

Example 3

ACE Expression Increases with Formation of SBS

To confirm microarray findings, real-time PCR analysis was performed (Table 2). These results similarly showed a significantly ($P<0.05$) increased expression of IEL-derived ACE in the SBS 1 w mouse group. Western immunoblotting (Table 2, FIG. 1) showed that ACE protein expression increased by 17% in the SBS group, although the change was not significant.

TABLE 2

Summary of results of ACE-inhibitor (ACE-I) studies. Sham + ACE-I was used as an additional control to assess the effects of ACE-I in the absence of a SBS. $^a$Results of real time PCR (results are expressed as the ratio of ACE-cDNA copies over β-actin-cDNA copies). $^b$Results of TUNEL analysis. Abbreviations: IEL, intraepithelial lymphocytes; ACE, angiotensin converting enzyme; EC, epithelial cells; TNF-α, tumor necrosis factor alpha. *P < 0.05 Sham vs. SBS, °P < 0.05 SBS vs. SBS + ACE-I, †P < 0.05 Sham vs. Sham + ACE-I.

| Group | IEL ACE mRNA$^a$ | IEL ACE protein | EC Apoptosis$^b$ (%) | Villus height (μm) | Crypt depth (μm) | IEL TNF-α mRNA |
|---|---|---|---|---|---|---|
| Sham | 0.22 ± 0.11 | 0.09 ± 0.02 | 3.6 ± 1.2 | 353 ± 40 | 77 ± 10 | 0.41 ± 0.13 |
| Sham + ACE-I | 0.66 ± 0.22† | 0.13 ± 0.01† | 1.9 ± 0.4† | 340 ± 20 | 87 ± 6 | 0.37 ± 0.07 |
| SBS | 0.49 ± 0.08* | 0.11 ± 0.01 | 4.3 ± 1.3 | 556 ± 66* | 113 ± 14* | 0.70 ± 0.19* |
| SBS + ACE-I | 0.63 ± 0.25 | 0.14 ± 0.03° | 1.8 ± 0.5° | 552 ± 56 | 145 ± 22° | 0.50 ± 0.07° |

Example 4

ACE Expression in IEL Subpopulation

IEL were sorted to determine if there was a differential expression of ACE in IEL sub-populations. IEL for this section were derived from adult, untreated mice. mRNA expression of ACE was detected in all sorted IEL sub-populations (Table 3). Although a greater expression of ACE was noted in the CD8α sub-population, no statistical difference was seen among groups.

Table 3. ACE MRNA expression in sorted IEL sub-populations. IEL were derived from adult, untreated mice. Note the fairly uniform expression of ACE in each subpopulation. Abbreviations: TCR, T-cell receptor.

| IEL Subpopulation | ACE mRNA Expression |
|---|---|
| αβ-TCR | 0.63 ± 0.01 |
| γδ-TCR | 0.57 ± 0.15 |
| CD4 | 0.77 ± 0.13 |
| CD8α | 0.86 ± 0.13 |

Example 5

Effect of ACE-I on EC Apoptosis, Histology and IEL ACE Expression

To further understand the relevance of ACE expression on EC apoptosis, ACE-inhibition was used. ACE-I (enalaprilat, 0.6 mg/kg/day i.p.) was given to both SBS (SBS+ACE-I), and sham operated (Sham+ACE-I) mice over a 7 day period, starting on the day after surgery. This latter group was studied as an additional control to assess the effects of ACE-I in the absence of a SBS. After 1 week, mice were killed, EC apoptotic rates assessed, and IEL mRNA and protein isolated.

Figure 2:
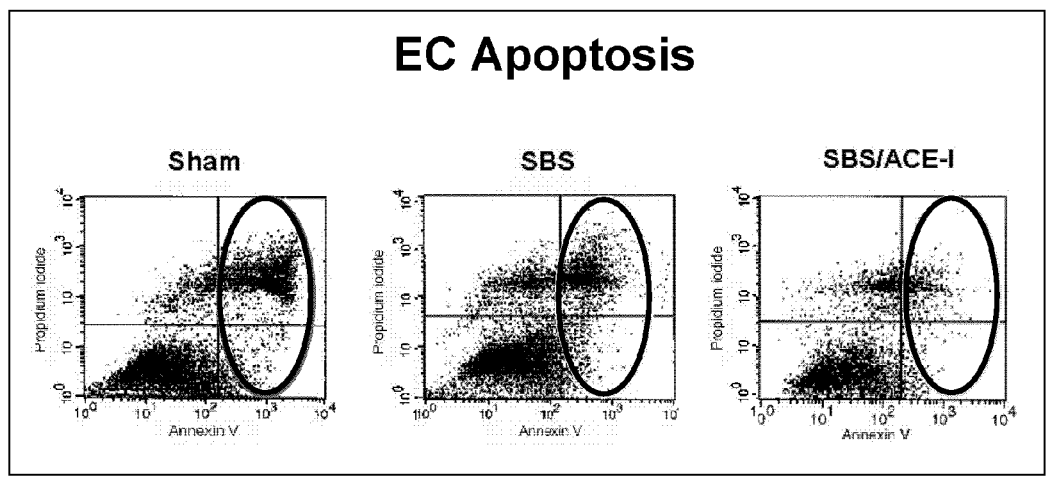
FIG. 2 depicts epithelial cell apoptosis in Sham mice (defined as mice undergoing a transaction of the mid-portion of the small bowel with no resection of intestine), SBS mice (defined as mice undergoing a massive (70%) small bowel resection, and SBS mice administered ACE inhibitors. For all figures, Enalaprilat was used as the angiotensin converting enzyme inhibitor (ACE-I), at a dose of 0.6 mg/kg/day intraperitoneally. Epithelial cell (EC) apoptosis is shown 1 week postoperatively in each group. In the Sham and SBS group EC apoptosis was significantly increased. With ACE-I administration a significant decrease in apoptosis was noted. Apoptosis was defined by Annexin V staining and detected with flow cytometry, whereby Annexin V positive cells denote apoptosis (circled quadrants), and propidium iodide positive cells denote cell necrosis. Note the marked reduction in apoptosis in the angiotensin converting enzyme inhibitor treated mice. Levels of apoptosis for each group are as follows: Sham: $39.9 \pm 5.7\%$; SBS: $36.0 \pm 19.9\%$; SBS/ACE-I $14.4 \pm 5.1\%$. The difference was significantly different (using ANOVA, with a least significant difference post-hoc testing) at the $P<0.01$, level.

Apoptosis: Annexin V staining: In the Sham and SBS groups EC apoptosis was significantly ($P<0.01$) increased (39.9±5.7% and 36.0±19.9%, respectively) compared to non-operated mice (14.4±5.1%)—a normal consequence of surgical resection. With ACE-I administration a significant decrease in apoptosis was noted in both Sham+ACE-I and SBS+ACE-I groups (16.9±8.8% and 13.1±4.5%, respectively) (FIG. 2). EC necrosis was also decreased in the enalaprilat treated mice. However, the differences were not significant between groups: Sham 11.6±7.1%, SBS 9.6±4.6, Sham+ACE-I 5.2±2.6%, SBS+ACE-I 5.2±2.6%.

TUNEL staining: As EC apoptosis rates tended to be high with Annexin V staining due to separation of EC tight junctions during the isolation process, a second, in situ method for measuring apoptosis was performed (Table 2). In the SBS+ACE-I-group the apoptotic rate declined by 58% compared to untreated SBS mice. In the Sham+ACE-I group EC apoptosis decreased by 48% compared to untreated Sham mice. Location of apoptotic cells was also altered with ACE-I administration. It was noted that apoptotic cells in SBS and Sham groups were distributed in both crypts and lower villi, whereas after administration with ACE-I apoptotic cells were confined to the crypts.

Figure 3:
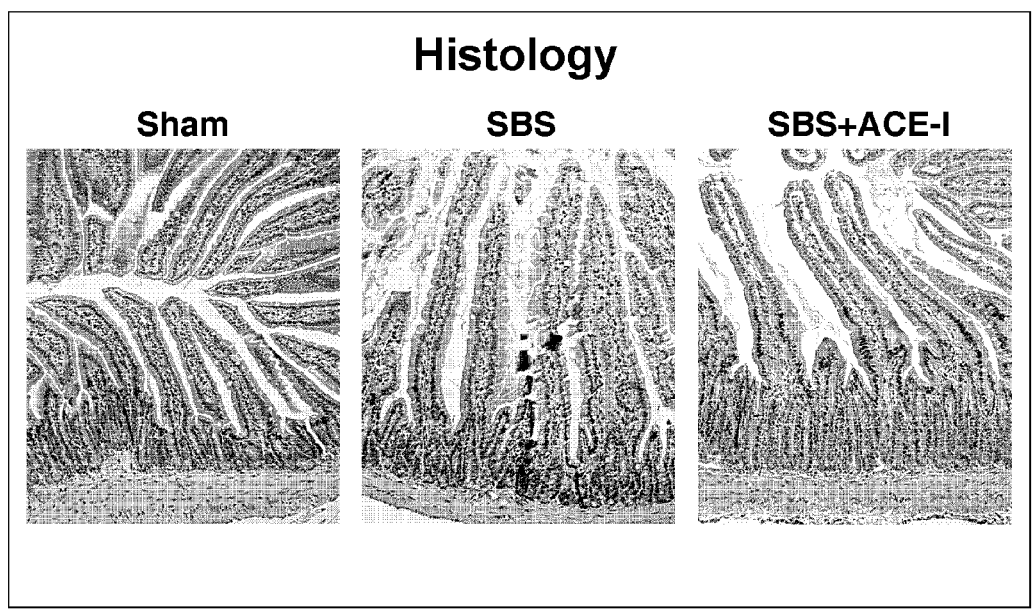
FIG. 3 depicts the one-week postoperative histology of Sham mice, SBS mice, and SBS mice administered ACE inhibitors. With ACE-I administration crypt depth significantly further increased, whereas villus height was unchanged. Magnification 160×. Mean villus heights in each group are as follows (expressed as μm±standard deviation): Sham: 353±40; SBS: 556±66*; Sham/ACE-I 340±20; SBS/ACE-I 552±56. Mean crypt depths in each group are as follows (expressed as μm±standard deviation): Sham: 77±10; SBS: 113±14*; Sham/ACE-I 87±6; SBS/ACE-I 145±22°. Although not shown in the figure, the Sham/ACE-I group depicts a separate group of Sham mice treated with ACE-I, and denotes that the action of ACE-I is most evident in mice with the disorder of short bowel syndrome (SBS). *P<0.05 Sham vs. SBS, °P<0.05 SBS vs. SBS+ACE-I, using analysis of variance. Note predominant action of ACE is in the increase of crypt depth—the key portion of the intestine for early-renewed intestinal growth.

Histology: SBS group villus height and crypt depth were significantly increased compared to Sham mice. ACE-I administration to SBS mice resulted in a significant (P=0.02), additional increase in crypt depth, whereas villus height was unchanged compared to SBS mice (Table 2, FIG. 3). Sham+ ACE-I mice showed no significant alterations in histological features.

Example 6

Role of ACE Inhibitors in EC Apoptosis

Figure 4:
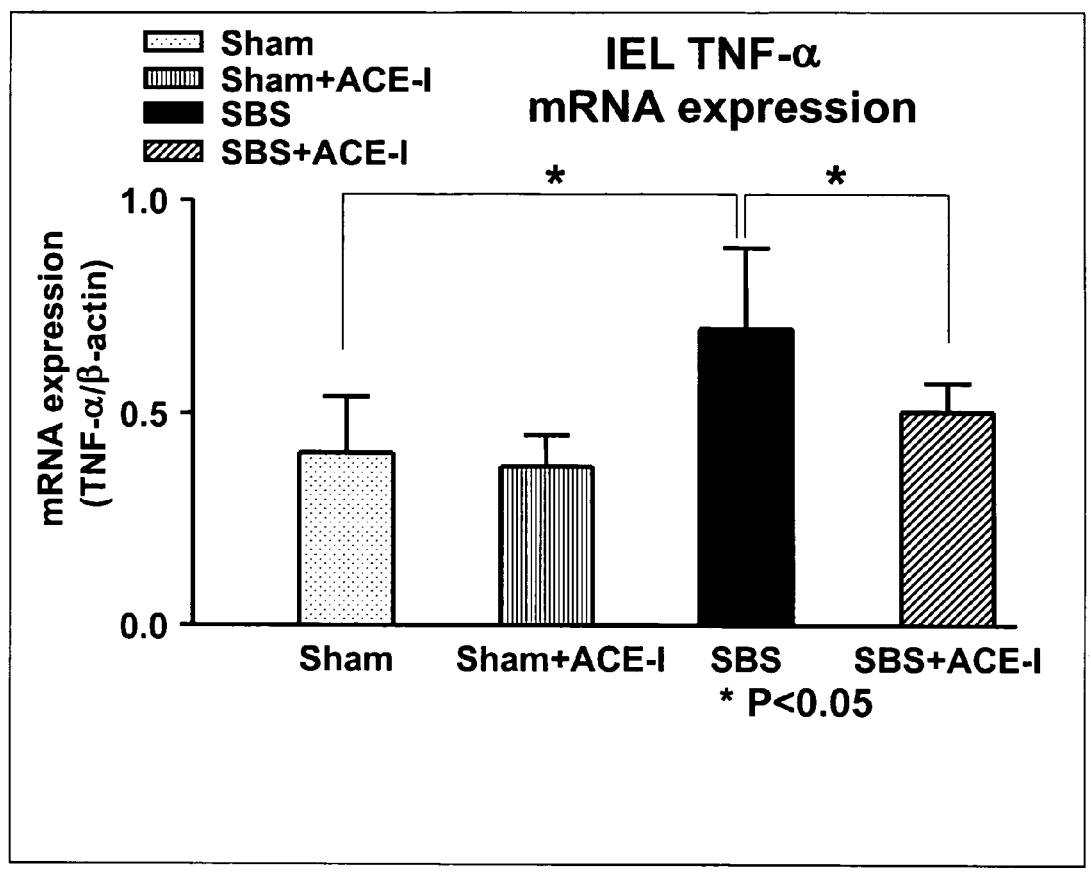
FIG. 4 depicts intraepithelial lymphocyte TNF-alpha mRNA expression in Sham mice, mice after massive small bowel resection, and mice with massive small bowel resection administered ACE inhibitors. TNF-α (tumor necrosis factor alpha) mRNA is expressed using polymerase chain reaction techniques. Statitical comparison of groups used analysis of variance with P<0.05 between marked groups.
Figure 11:
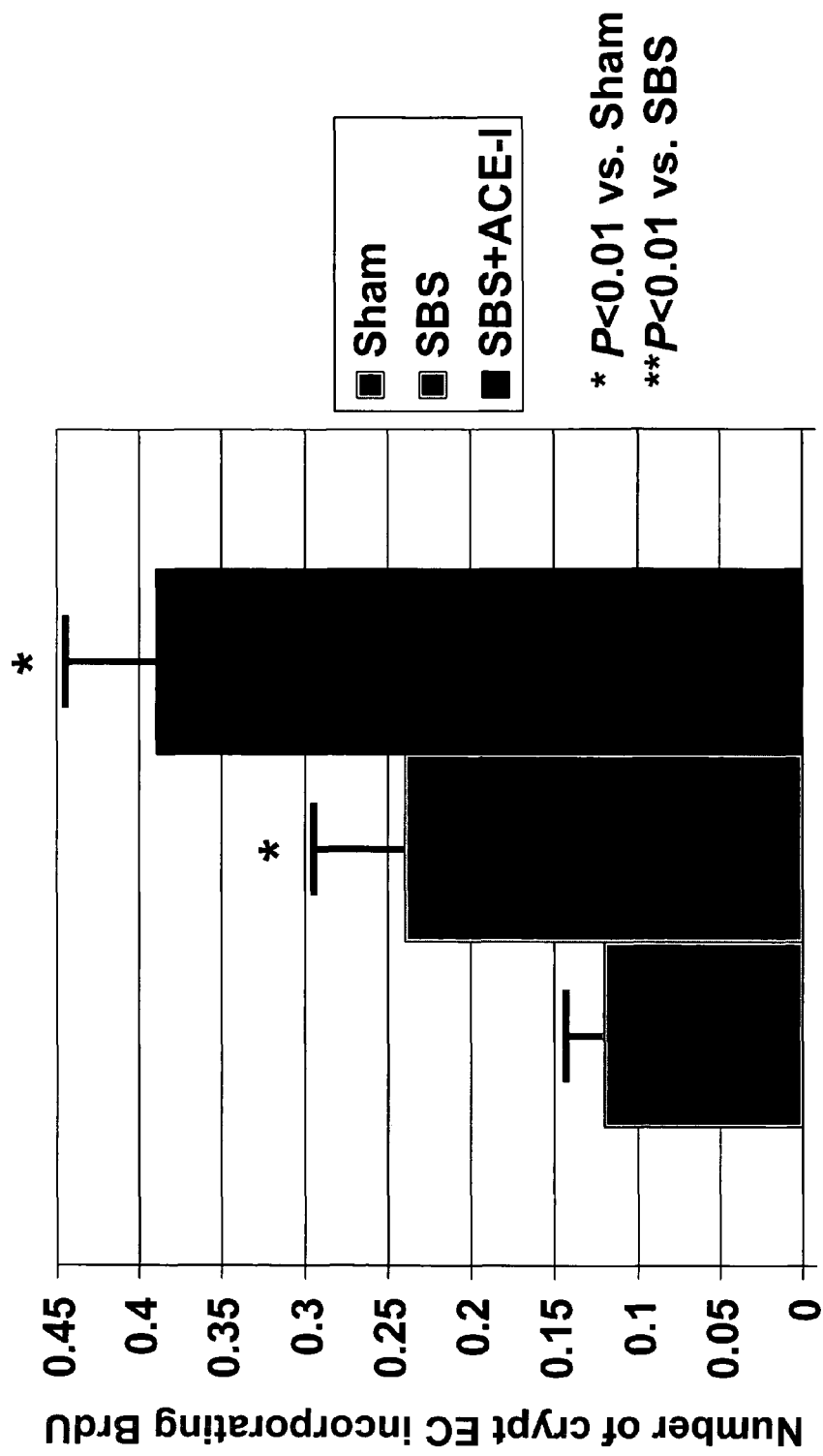
FIG. 11 shows an increase in intestinal epithelial cell proliferation with the use of ACE-inhibitor enalaprilat in a short bowel syndrome model.

FIG. 4 shows that administration of ACE-I leads to a decreased expression of TNF-α. ACE inhibitors (enalaprit) inhibit the expression of TNF-a. Thus, ACE inhibitors when provided to a subject (e.g., via oral or rectal administration) inhibit the rate of colonic mucosal epithelial cell apoptosis. ACE inhibitors also increase the rate of colonic mucosal epithelial cell proliferation. Furthermore, epithelial cell proliferation was observed to increase significantly with the administration of ACE-I (See FIG. 11).

Example 7

Effects on Colitis

Male C57BL/6 specific-pathogen-free 2-month-old mice were kept in a 12-hour day/night environment maintained at 23° C. and a relative humidity of 40-60%. All mice drank 2.5% (w/v) DSS in water for 7 days followed by one day of plain water, while being fed normal mouse chow. Mice either received daily enalaprilat injection (0.015 mg/day, injection volume 0.5 ml, intraperitoneal) (n=6, "ACE-I") or daily normal saline injection 0.5 ml (n=6, "Saline"). Body weight and hemoccult stool reaction were recorded. After the eight days of treatment, mice were euthanized with $CO_2$, and colonic samples were immediately taken for histology and mucosal RNA extraction. Distal 1-cm colonic segments were excised, opened longitudinally, and fixed in 10% neutral buffered formalin. The remainder of the colon, including the cecum, was washed, cut into pieces, and mixed gently at 37° C. in EDTA/dithiothreitol buffer. The resulting mixture of epithelial cells and intraepithelial lymphocytes was then filtered through nylon wool and pelleted by centrifugation. Total RNA of the cell pellet was obtained using TRIZOL reagent and chloroform-isopropanol-ethanol extraction. Reverse transcription of RNA was done in the presence of RNAse inhibitor. RT product was then amplified with forward and reverse primers specific for ACE, TNF-α, and beta-actin, using real-time semiquantitative PCR. PCR results were analyzed by expressing ACE and TNF-α levels as a ratio to beta-actin levels, and were compared using a 2-tailed students' T test. Histologic grading of colitis was done by blinded observers using a standard scale for colitis severity. Histologic scores, as well as body weights and hemoccult results, were compared between groups using a 2-tailed homoscedastic T test.

Figure 5:
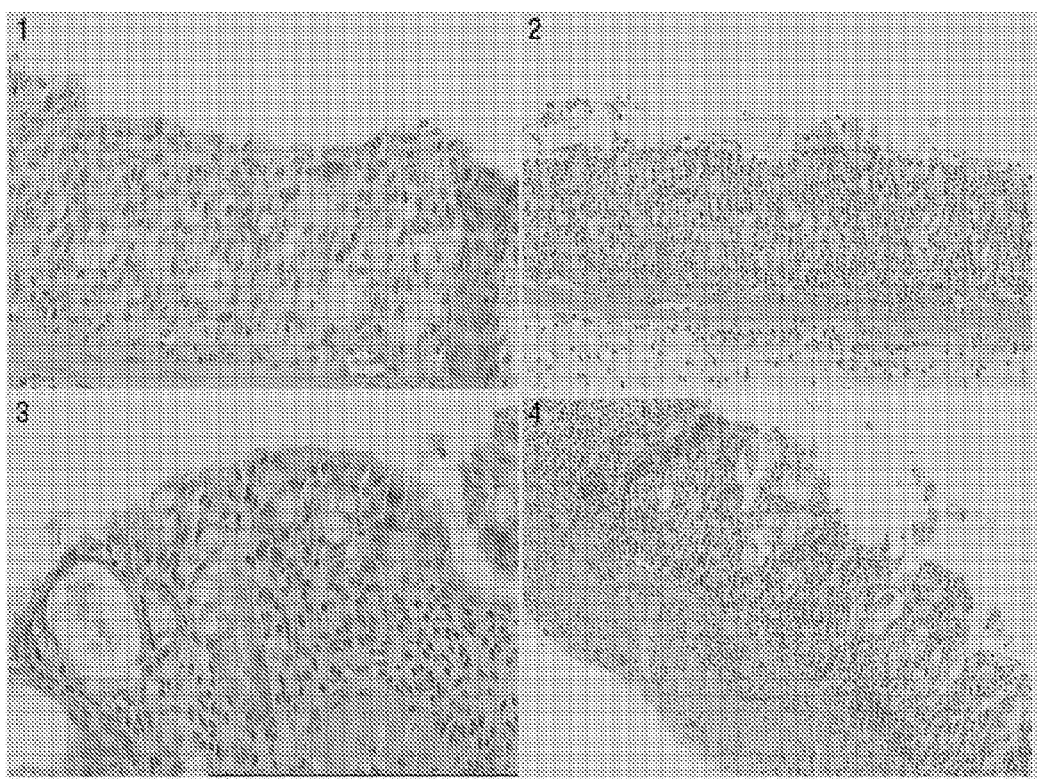
FIG. 5 depicts changes in the histology of a mouse inflammatory bowel disease model. Mice were fed DSS for a 5-day period. This well established model induces a colitis (i.e., inflammation of the colon). In this setting, one group of mice were additionally given the angiotensin converting enzyme—Enalaprilat, the other group (Control group) were given saline as a control. The histomicrographs show a more severe degree of colitis in the Control group. In images 1 and 2 (DSS-saline images 1 and 2) representative images from DSS-induced colitis treated only with saline injection are shown, at 200× and 100× magnification. Note the essentially complete loss of all colonic mucosal crypts and nearly complete loss of surface epithelial cells. This corresponds grossly to areas of ulceration in this model. Images 3 and 4 (ACE-I images 1 and 2) depict samples of mice with DSS colitis treated with daily enalaprilat injection, at 200× and 100× magnification, respectively. Note that while there are areas of ulcerative mucosa, there are also significant areas retaining colonic crypts as well as surface epithelial cells.
Figure 6:
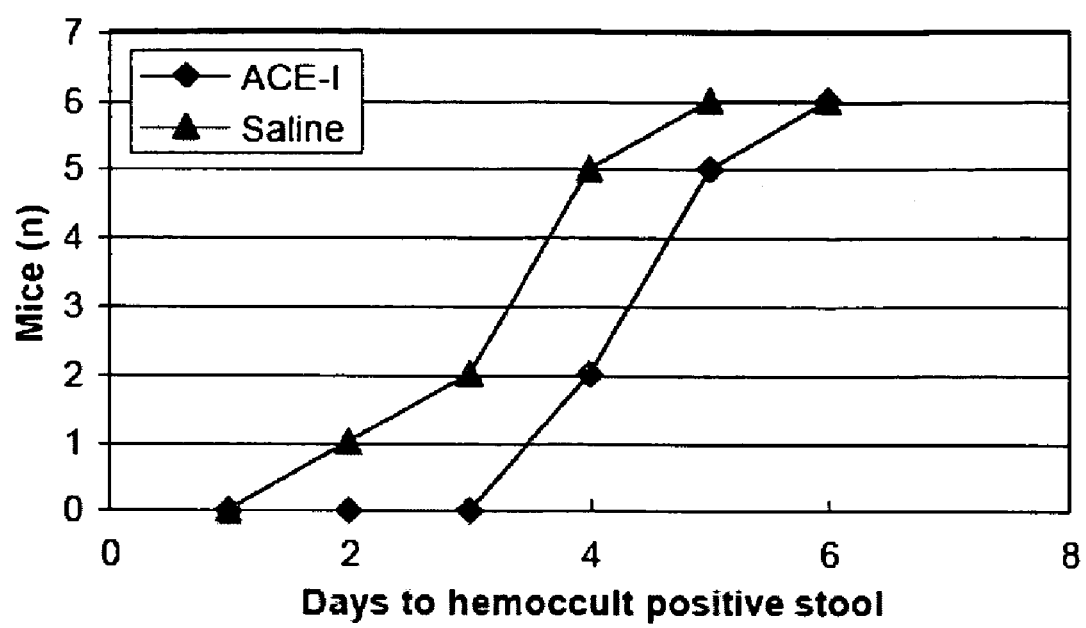
FIG. 6 shows that the time course of development of heme-positive stools in mice treated with ACE-I was significantly delayed in comparison to mice treated only with saline injection.

The clinical severity of colitis was improved by administration of ACE-I (FIG. 5 and Table 4) as shown by a significant prevention in loss of body weight, and a delay in the development of heme-positive stools. The time course of colitis is demonstrated in FIG. 6. ACE-I mice also showed significantly improved histologic colitis scores (12.6±1.6 vs. 14.8±1.3, p<0.01) (FIG. 5). These scores correspond to a uniformly severe ulcerative mucosal loss in Saline mice, but with partial sparing of colonic epithelium in ACE-I mice. Mucosal ACE levels were reduced in ACE-I mice (expressed in the table as a ratio to beta-actin levels).

Table 4. Results of outcomes in the two groups of mice: DSS treated with either saline (DSS+Saline, Control group) or DSS treated with ACE-inhibitors (DSS+ACE-I). Note the statistically significant improvement in clinical outcomes of body weight loss, and onset of hemocult positive stools in the ACE-I group. Additionally, note the significant improvement in histologic grade in the ACE-I treated group.

| Groups | Body Weight Loss (%) | Hemocult onset (days) | Histologic Grade | ACE levels (mRNA) |
|---|---|---|---|---|
| DSS + Saline | 23.7 ± 4.2 | 3.7 ± 1.0 | 14.7 ± 1.4 | 4.07 ± 4.71 |
| DSS + ACE-I | 16.6 ± 2.7 | 4.8 ± 0.8 | 11.8 ± 1.5 | 0.08 ± 0.13 |
| P level | <0.01 | <0.05 | <0.01 | <0.05, one tailed |

Example 8

Compositions Comprising an ACE Inhibitor and Polyethylene Glycol and Methods of Use Thereof The present invention provides a unique compound comprising an ACE inhibitor (e.g., Enalaprilat) and polyethylene glycol (e.g., 1000 molecular weight). In some embodiments, the ACE inhibitor is suspended in the polyethylene glycol. Polyethylene glycol is a relative non-inert carrier. This compound can be directly administered (e.g., rectally via an enema) to a subject in order to treat (e.g., both therapeutically and prophylactically) inflammatory bowel disease (e.g., colitis due to ulcerative colitis or Crohn's disease). It is contemplated that the direct administration (e.g., via an enema) provides a significant benefit to subjects who suffer from the adverse effects of immunosuppression of steroids and other agents which act systemically on the immune system.

Example 9

Figure 7:
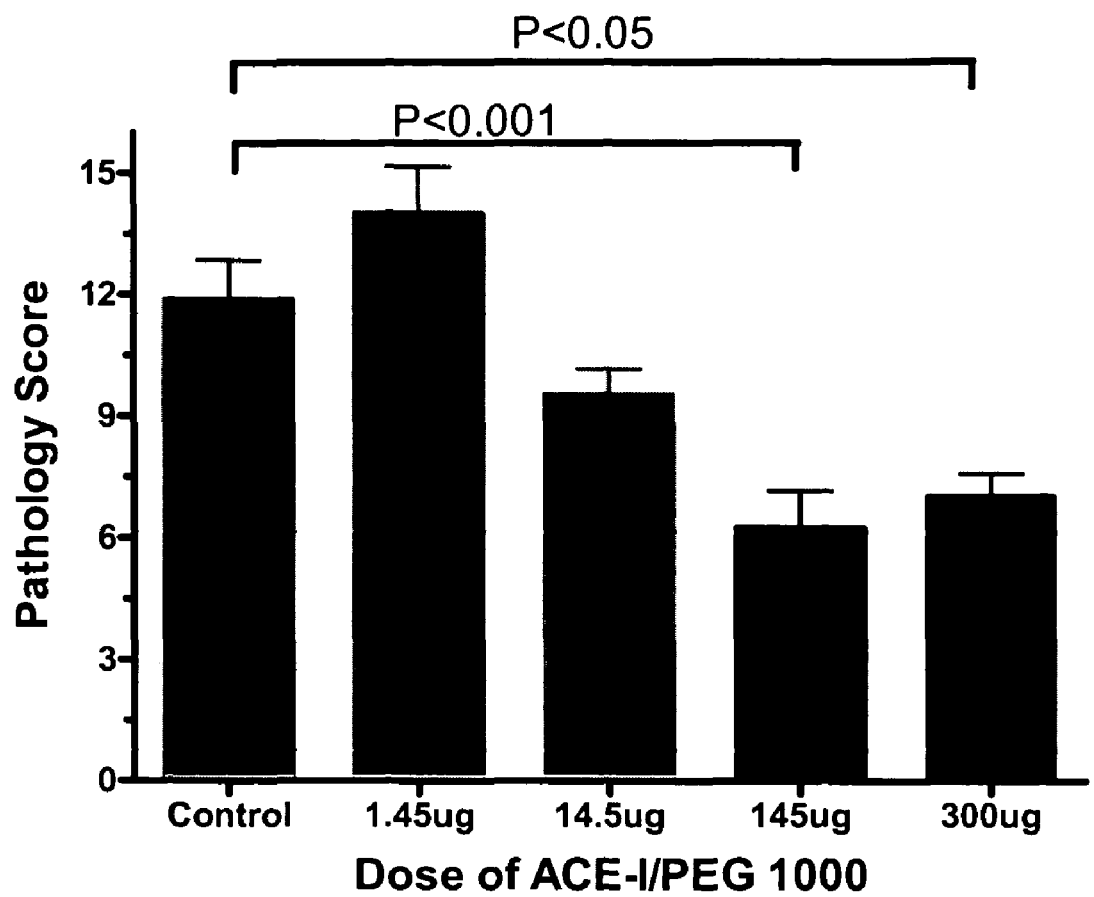
FIG. 7 shows the pathology score of mice with colitis administered a composition comprising the ACE-inhibitor enalaprilat at various doses in PEG 1000.

Administration of a Composition Comprising an ACE-Inhibitor and PEG to a Mouse with Colitis Significantly Reduces Pathology in the Mouse In order to determine if administration of an ACE-inhibitor in polyethylene glycol could reduce the severity of colitis (e.g., signs and symptoms of colitis), a mouse model of colitis was examined. The ACE-inhibitor enalaprilat in polyethylene glycol 1000 was administered via an enema to a mouse with colitis. Each group of mice were treated with dextran sodium sulfate. Treatment groups were given a daily enema of enalaprilat at varying doses combined with polyethylene glycol (PEG) 1000 molecular weight (See FIG. 7). Analysis is done with ANOVA and a Bonferroni post-hoc analysis of groups. There was nearly a 2-fold decline in the severity of the pathology score in the two highest treated groups of mice compared to controls.

Example 10

Administration of a Composition Comprising an ACE-Inhibitor and PEG to a Mouse with Colitis Significantly Reduces the Expression of Tumor Necrosis Factor Alpha (TNF-α) and Interleukin 1b (IL-1b)

Figure 8:
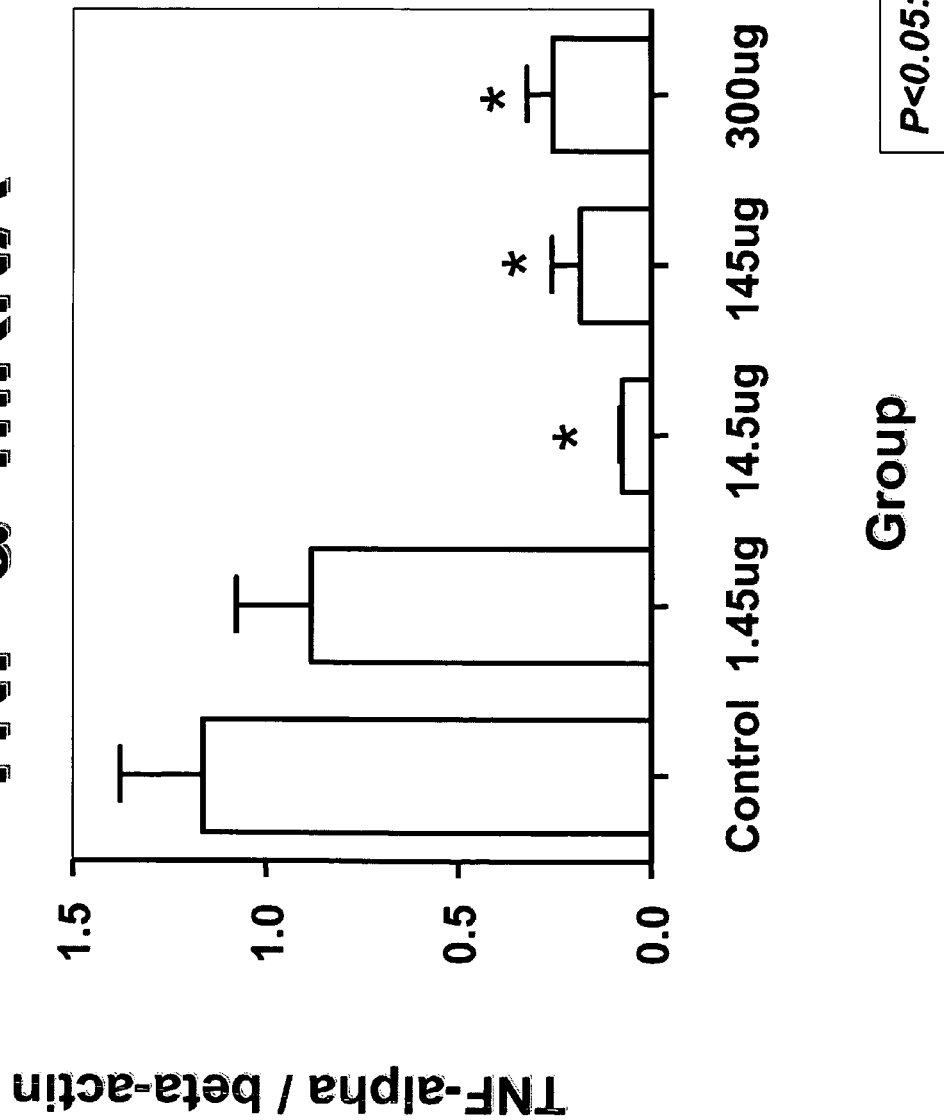
FIG. 8 shows a decreased expression of tumor necrosis factor alpha when ACE-inhibitor enalaprilat suspended in PEG-1000 is given daily to a mouse model of ulcerative colitis.
Figure 9:
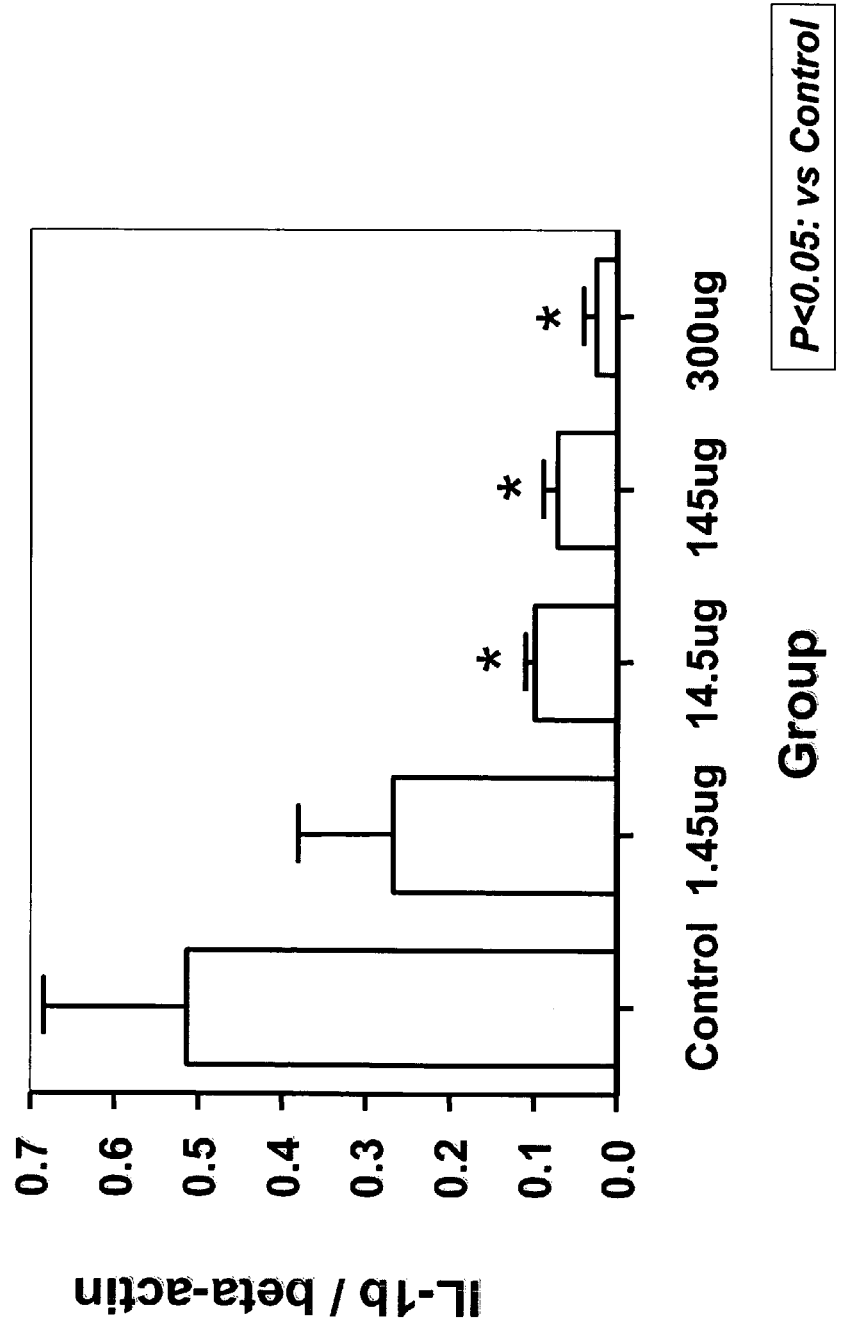
FIG. 9 shows decreased expression of interleukin-1b when ACE-inhibitor enalaprilat suspended in PEG-1000 is given daily to a mouse model of ulcerative colitis.

The administration of a composition comprising an ACE-inhibitor and PEG to a mouse with colitis resulted in a decreased expression of two pro-inflammatory cytokines, TNF-α and IL-1b (See FIGS. 8 and 9). Although an understanding of the mechanism is not necessary to practice the present invention and the present invention is not limited to any particular mechanism of action, in some embodiments, a composition comprising an ACE-inhibitor and PEG compound mediate a decrease in the signs and symptoms of inflammatory bowel disease (e.g., colitis) due to a decrease in TNF-α and/or IL-1b expression and/or activity in a subject administered a composition comprising an ACE-inhibitor and PEG compound.

Example 11

Figure 10:
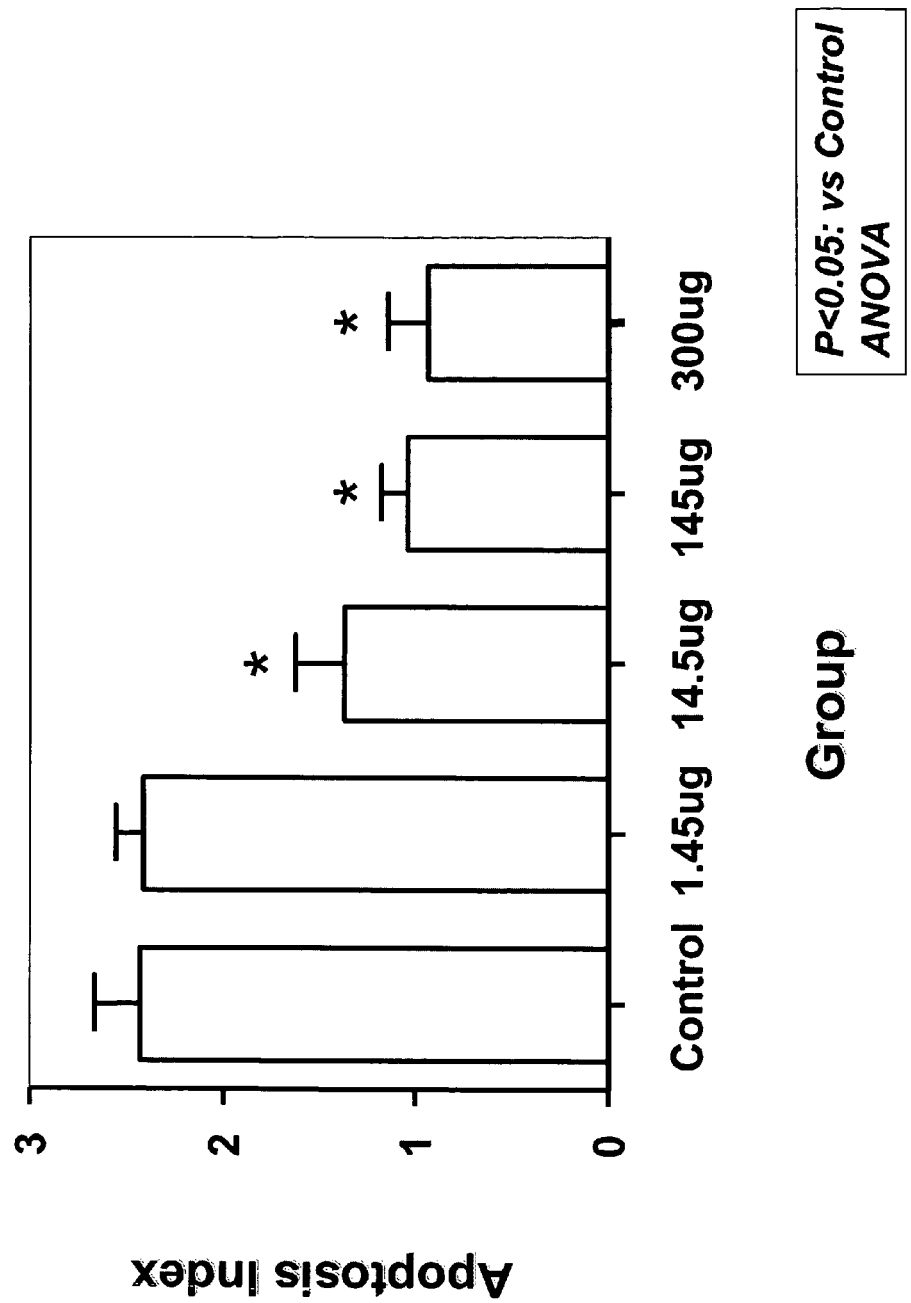
FIG. 10 shows a decreased occurrence of epithelial cell apoptosis when ACE-inhibitor enalaprilat suspended in PEG-1000 is given daily to a mouse model of ulcerative colitis.

Administration of a Composition Comprising an ACE-Inhibitor and PEG to a Mouse with Colitis Significantly Reduces the Occurrence of Epithelial Cell Apoptosis The administration of a composition comprising an ACE-inhibitor and PEG to a mouse with colitis results in a significantly decreased development of epithelial cell apoptosis—a major mechanism by which the mucosa is destroyed in inflammatory conditions of the intestine (See FIG. 10). Thus, although an understanding of the mechanism is not necessary to practice the present invention and the present invention is not limited to any particular mechanism of action, in some embodiments, a composition comprising an ACE-inhibitor and PEG compound mediate a decrease in the signs and symptoms of inflammatory bowel disease (e.g., colitis) due to a reduction in the occurrence of epithelial cell apoptosis in a subject administered a composition comprising an ACE-inhibitor and PEG compound.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A method of therapeutically treating a subject, comprising:
   a) providing:
      i) a subject with inflammatory bowel disease, and
      ii) a composition comprising enalaprilat and polyethylene glycol, and;
   b) enterally administering a therapeutically effective dose of said composition to said subject under conditions such that the severity of inflammatory bowel disease is reduced in said subject.

2. The method of claim 1, wherein said polyethylene glycol is 1000 molecular weight.

3. The method of claim 1, wherein said composition is co-administered with a corticosteroid.

4. The method of claim 3, wherein said corticosteroid is prednisone.

5. The method of claim 1, wherein said composition is administered rectally.

6. The method of claim 5, wherein administering rectally comprises an enema.

7. The method of claim 1, wherein said inflammatory bowel disease is selected from the group consisting of Crohn's disease, celiac disease, ulcerative colitis, diverticulitis, pouchitis, or chronic diarrhea.

8. The method of claim 1, wherein reduction of the severity of inflammatory bowel disease in said subject is detectable by a decrease in the clinical severity of colitis in said subject.

9. The method of claim 1, wherein reduction of the severity of inflammatory bowel disease in said subject is detectable by the absence of the loss of body weight in said subject.

10. A method of therapeutically treating a subject, comprising:
    a) providing:
       i) a subject with inflammatory bowel disease, and
       ii) a composition comprising enalaprilat and polyethylene glycol, and;
    b) enterally administering, by other than aerosol delivery, a therapeutically effective dose of said composition to said subject under conditions such that the severity of inflammatory bowel disease is reduced in said subject.

11. The method of claim 10, wherein said composition is co-administered with a corticosteroid.

12. The method of claim 11, wherein said corticosteroid is prednisone.

13. The method of claim 10, wherein said composition is administered rectally.

14. The method of claim 13, wherein administering rectally comprises an enema.

15. The method of claim 10, wherein said inflammatory bowel disease is selected from the group consisting of Crohn's disease, celiac disease, ulcerative colitis, diverticulitis, pouchitis, or chronic diarrhea.

16. The method of claim 10, wherein reduction of the severity of inflammatory bowel disease in said subject is detectable by a decrease in the clinical severity of colitis in said subject.

17. The method of claim 10, wherein reduction of the severity of inflammatory bowel disease in said subject is detectable by the absence of the loss of body weight in said subject.

* * * * *